US008891729B2

(12) United States Patent
Matoba et al.

(10) Patent No.: US 8,891,729 B2
(45) Date of Patent: Nov. 18, 2014

(54) X-RAY ANALYZER AND X-RAY ANALYSIS METHOD

(75) Inventors: Yoshiki Matoba, Chiba (JP); Rintaro Nakatani, Chiba (JP); Tsuneo Sato, Chiba (JP)

(73) Assignee: SII NanoTechnology Inc. (JP)

( * ) Notice: Subject to any disclaimer, the term of this patent is extended or adjusted under 35 U.S.C. 154(b) by 189 days.

(21) Appl. No.: 13/564,800

(22) Filed: Aug. 2, 2012

(65) Prior Publication Data
US 2013/0034204 A1 Feb. 7, 2013

(30) Foreign Application Priority Data
Aug. 5, 2011 (JP) .................................. 2011-171595

(51) Int. Cl.
*G01N 23/223* (2006.01)
*G01N 23/06* (2006.01)

(52) U.S. Cl.
CPC .............. *G01N 23/06* (2013.01); *G01N 23/223* (2013.01)
USPC .................................. 378/46; 378/53; 378/58

(58) Field of Classification Search
CPC ... G01N 23/06; G01N 23/18; G01N 23/2204; G01N 23/223; G01N 2223/04; G01N 2223/71; G01N 2223/76; G01N 2223/309
USPC ................................ 378/44, 45, 46, 57, 53, 58
See application file for complete search history.

(56) References Cited

U.S. PATENT DOCUMENTS 6,839,406 B2 * 1/2005 Ries et al. ....................... 378/70
2006/0098773 A1 * 5/2006 Peschmann ..................... 378/57

FOREIGN PATENT DOCUMENTS

JP          2003057195          2/2003

* cited by examiner

*Primary Examiner* — Glen Kao
(74) *Attorney, Agent, or Firm* — Adams & Wilks

(57) ABSTRACT

An X-ray analyzer includes a transmission X-ray inspecting portion having a first X-ray source and a transmission X-ray detector for detecting a transmission X-ray that passed through a sample from the first X-ray source, and a fluorescent X-ray inspecting portion having a second X-ray source and a fluorescent X-ray detector for detecting a fluorescent X-ray output from the sample when the sample is irradiated with an X-ray from the second X-ray source. A movement mechanism moves a sample stage that supports the sample. A foreign matter position calculating unit calculates a position of foreign matter in the sample, and a movement mechanism control unit controls the movement mechanism so that the position of the foreign matter calculated by the foreign matter position calculating unit coincides with an optical axis of the second X-ray source.

3 Claims, 4 Drawing Sheets

X-RAY ANALYZER AND X-RAY ANALYSIS METHOD

BACKGROUND OF THE INVENTION

1. Field of the Invention

The present invention relates to an X-ray analyzer and an X-ray analysis method, which are capable of measuring both a transmission X-ray and a fluorescent X-ray.

2. Description of the Related Art

Conventionally, a foreign matter in a sample and density unevenness of elements have been detected by X-ray transmission imaging. On the other hand, the kinds of elements of the foreign matter and the like cannot be identified through the X-ray transmission imaging, and hence, a sample has been analyzed for elements through use of a fluorescent X-ray analysis.

Further, an analyzer capable of solely performing both a transmission X-ray analysis and a fluorescent X-ray analysis has also been developed (Japanese Patent Application Laid-open No. 2003-57195).

By the way, for example, a positive electrode active material (lithium salt) of a lithium ion battery or the like is produced by being thinly pasted to a collector, and the quality of a positive electrode active material layer is managed as follows. First, the presence/absence of a foreign matter in a positive electrode active material layer is analyzed by a transmission X-ray apparatus. When a foreign matter is detected, the position of the foreign matter in the sample is marked, and the sample is set on a separate fluorescent X-ray apparatus to identify the kind of an element in the foreign matter.

However, the work of marking the position of a foreign matter detected by the transmission X-ray apparatus and irradiating the marked position with an X-ray through use of a separate fluorescent X-ray apparatus with exact alignment is very cumbersome, and may cause a positional misalignment. Thus, the analysis requires time and labor, and the analysis accuracy is not high.

Further, in the case of the technology described in Japanese Patent Application Laid-open No. 2003-57195, the entire surface of a sample is subjected to a transmission X-ray analysis and a fluorescent X-ray analysis. However, it is not necessary to subject a part of the sample other than a part including a foreign matter to an element analysis through use of a fluorescent X-ray. Thus, the technology requires a longer time for analysis and is not suitable for a rapid analysis.

SUMMARY OF THE INVENTION

The present invention has been made to solve the above-mentioned problems, and provide an X-ray analyzer and an X-ray analysis method, which are capable of accurately and rapidly analyzing elements, through use of a fluorescent X-ray, at a position of a foreign matter detected by a transmission X-ray apparatus.

According to an exemplary embodiment of the present invention, there is provided an X-ray analyzer, including: a transmission X-ray inspecting portion including: a first X-ray source; and a transmission X-ray detector for detecting a transmission X-ray having passed through a sample from the first X-ray source; a fluorescent X-ray inspecting portion including: a second X-ray source; and a fluorescent X-ray detector for detecting a fluorescent X-ray output from the sample when the sample is irradiated with an X-ray from the second X-ray source; a sample stage for holding the sample; a movement mechanism for moving the sample stage relatively between an irradiation position of the first X-ray source and an irradiation position of the second X-ray source; foreign matter position calculating means for calculating a position of a foreign matter detected in the sample by the transmission X-ray detector; and movement mechanism control means for controlling the movement mechanism so that the position of the foreign matter calculated by the foreign matter position calculating means coincides with an optical axis of the second X-ray source.

According to the X-ray analyzer, the position of the foreign matter detected by the transmission X-ray inspection portion can be accurately and automatically irradiated with the X-ray from the second X-ray source, and the foreign matter can be analyzed for elements rapidly by the fluorescent X-ray inspecting portion.

It is preferred that an optical axis of the first X-ray source and the optical axis of the second X-ray source be parallel to each other, and a movement direction of the sample stage be perpendicular to the optical axes.

According to the above-mentioned configuration, the displacement in a direction perpendicular to the movement direction of the sample stage becomes zero. Therefore, even when the sample stage is moved, the distance in the vertical direction between the first X-ray source and the sample and the distance in the vertical direction between the second X-ray source and the sample can be invariably maintained at preset optimum values, and hence the measurement accuracy is not varied. Further, it is not necessary to provide a movement mechanism in the vertical direction.

The foreign matter position calculating means is configured to: calculate a distance $t2$ on the transmission X-ray detector along a direction perpendicular to an optical axis of the first X-ray source from the optical axis of the first X-ray source to the position of the foreign matter, a distance $h1$ parallel to the optical axis of the first X-ray source from the first X-ray source to the position of the foreign matter, and a distance $h2$ parallel to the optical axis of the first X-ray source from the first X-ray source to a position of the transmission X-ray detector; and calculate a distance $t1$ along a direction perpendicular to the optical axis of the first X-ray source from the optical axis of the first X-ray source to the position of the foreign matter based on an equation $t1=(h1/h2) \times t2$. In this manner, the distance $t1$ can be determined accurately.

According to an exemplary embodiment of the present invention, there is provided an X-ray analysis method, including: detecting a transmission X-ray having passed through a sample from a first X-ray source; detecting, at a position different from an irradiation position of the first X-ray source, a fluorescent X-ray output from the sample when the sample is irradiated with an X-ray from a second X-ray source; calculating a position of a foreign matter detected in the sample in the detecting a transmission X-ray; and moving the sample so that the position of the foreign matter coincides with an optical axis of the second X-ray source in the detecting a fluorescent X-ray.

According to the present invention, it is possible to accurately and rapidly analyze elements, through use of a fluorescent X-ray, at a position of a foreign matter detected by a transmission X-ray apparatus.

DETAILED DESCRIPTION OF THE PREFERRED EMBODIMENT

Hereinafter, an embodiment of the present invention is described with reference to the drawings.

Figure 1:
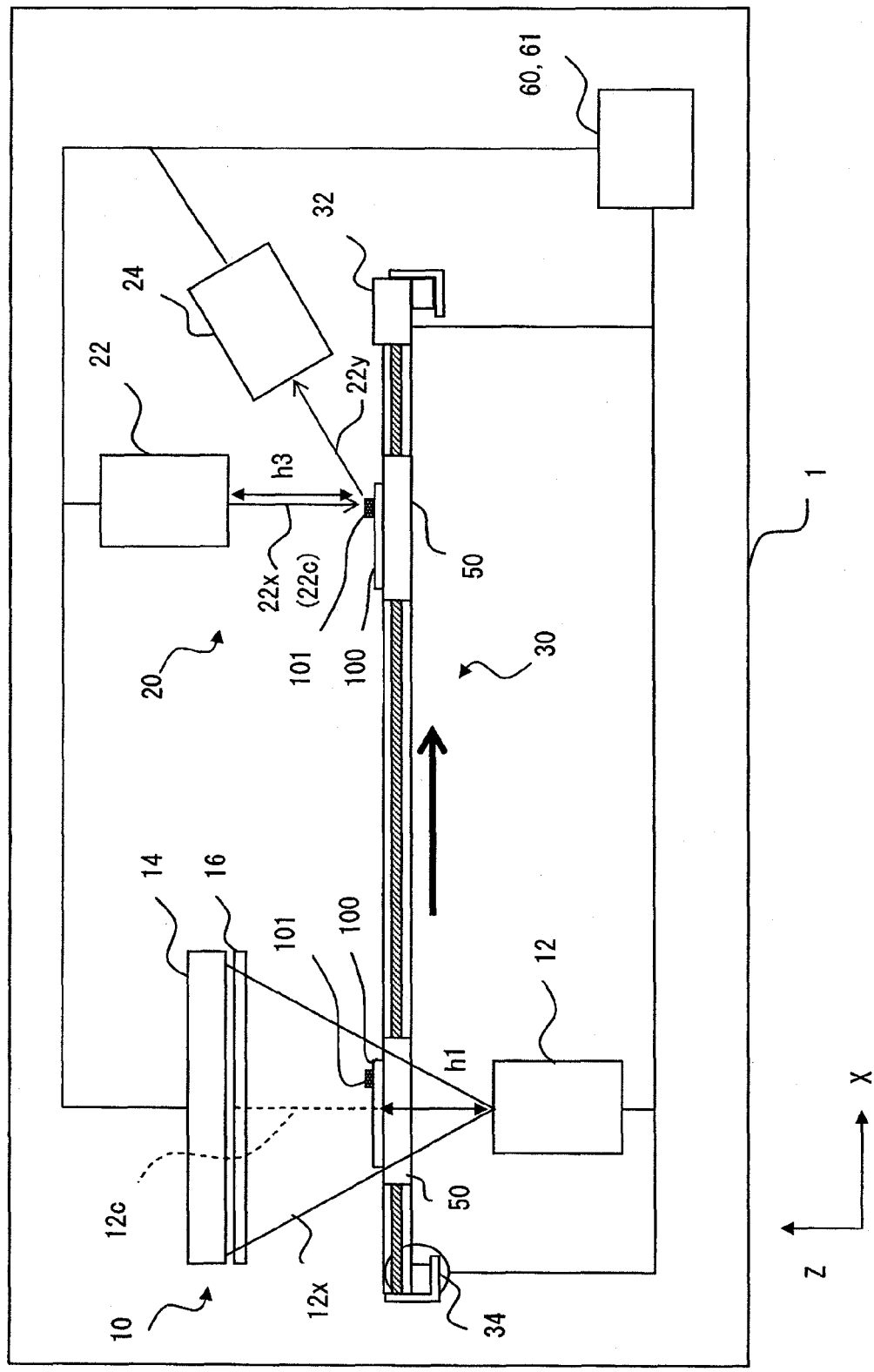
FIG. 1 is a block diagram illustrating a configuration of an X-ray analyzer according to an embodiment of the present invention.

FIG. 1 is a block diagram illustrating a configuration of an X-ray analyzer 1 according to the embodiment of the present invention.

The X-ray analyzer 1 includes: a transmission X-ray inspecting portion 10 including a first X-ray source 12 and a transmission X-ray detector 14; a fluorescent X-ray inspecting portion 20 including a second X-ray source 22 and a fluorescent X-ray detector 24; a sample stage 50 for holding a sample 100; a movement mechanism 30 for moving the sample stage 50 relatively between an irradiation position of the first X-ray source 12 and an irradiation position of the second X-ray source 22; foreign matter position calculating means 60 for calculating a position of a foreign matter 101 detected in the sample by the transmission X-ray detector 14; and movement mechanism control means 61 for controlling the movement mechanism 30.

Herein, the first X-ray source 12 is disposed below the sample 100. An X-ray is emitted upward from the first X-ray source 12 to pass through the sample 100 and is then converted into a visible light image through a fluorescent screen 16. Then, the visible light image is received by the transmission X-ray detector 14 disposed above the sample 100. The sample 100 is, for example, a chip of a lithium cobaltate electrode plate to be used in a positive electrode of a lithium ion battery.

Further, the second X-ray source 22 is disposed above the sample 100. An X-ray is emitted downward from the second X-ray source 22, and thereafter, the X-ray output from the sample 100 is detected by the fluorescent X-ray detector 24 disposed above the sample 100. The fluorescent X-ray detector 24 is obliquely disposed at a position having an angle with respect to an optical axis 22c of the second X-ray source 22.

The foreign matter position calculating means 60 and the movement mechanism control means 61 are implemented by a computer. The foreign matter position calculating means 60 and the movement mechanism control means 61 include a CPU, a ROM, a RAM, and the like, and are capable of executing predetermined computer programs, and also perform the overall processing such as the irradiation of X-rays from the X-ray sources 12 and 22 and detection by the transmission X-ray detector 14 and the fluorescent X-ray detector 24.

The first X-ray source 12 includes a predetermined X-ray tubular bulb. The X-ray tubular bulb, for example, emits as a primary X-ray an X-ray, which is generated by the fact that thermoelectrons generated from a filament (negative electrode) of the tubular bulb are accelerated by a voltage applied between the filament (negative electrode) and a target (positive electrode) to thereby smash against the target (tungsten (W), molybdenum (Mo), chromium (Cr), or the like), from a window of a beryllium foil or the like.

The transmission X-ray detector 14 is an area sensor including a plurality of semiconductor detection devices (solid-state image pickup devices or the like), which are arranged in a two-dimensional array. Examples of each solid-state image pickup device include a charge-coupled device (CCD) and a CMOS image sensor. A transmission X-ray 12$x$ having passed through the sample 100 is converted into fluorescent light (visible light image) by the fluorescent screen 16 and received by the transmission X-ray detector 14.

Note that, the first X-ray source 12 irradiates the entire sample 10 with an X-ray, and the transmission X-ray 12$x$ is detected by the transmission X-ray detector 14 that is an area sensor. Accordingly, a two-dimensional image of the sample 100 in a plane direction thereof is obtained at a time. However, for example, the sample 100 may be scanned in one direction to obtain a two-dimensional image, through use of a line sensor as the transmission X-ray detector 14.

The second X-ray source 22 includes a predetermined X-ray tubular bulb. As targets, W, Rh, Mo, and the like are used. The fluorescent X-ray detector 24 detects a fluorescent X-ray 22$y$ output from the sample 100 when the sample 100 is irradiated with an X-ray 22$x$ from the second X-ray source 22. The fluorescent X-ray detector 24 detects the fluorescent X-ray and a scattered X-ray output from (the foreign matter 101 of) the sample 100, and outputs a signal containing energy information of the fluorescent X-ray and the scattered X-ray. The fluorescent X-ray detector 24, for example, includes a semiconductor detection device (for example, silicon (Si) device which is a pin-structure diode) (not shown) disposed to an incident window of the X-ray, and when one X-ray photon enters, a current pulse corresponding to the one X-ray photon is output. An instantaneous current value of the current pulse is proportional to energy of the incident characteristic X-ray. Further, the fluorescent X-ray detector 24 is set so as to convert the current pulse output in the semiconductor detection device into a voltage pulse and amplify and output the voltage pulse as a signal. Note that, an analyzer (not shown) is connected to the fluorescent X-ray detector 24 to analyze the above-mentioned signal. The analyzer is, for example, a pulse height analyzer (multi-channel analyzer) for obtaining a pulse height of the voltage pulse from the signal to output an energy spectrum. Note that, a wavelength-dispersive fluorescent X-ray (WDX) detector 24 may be used.

Figure 2:
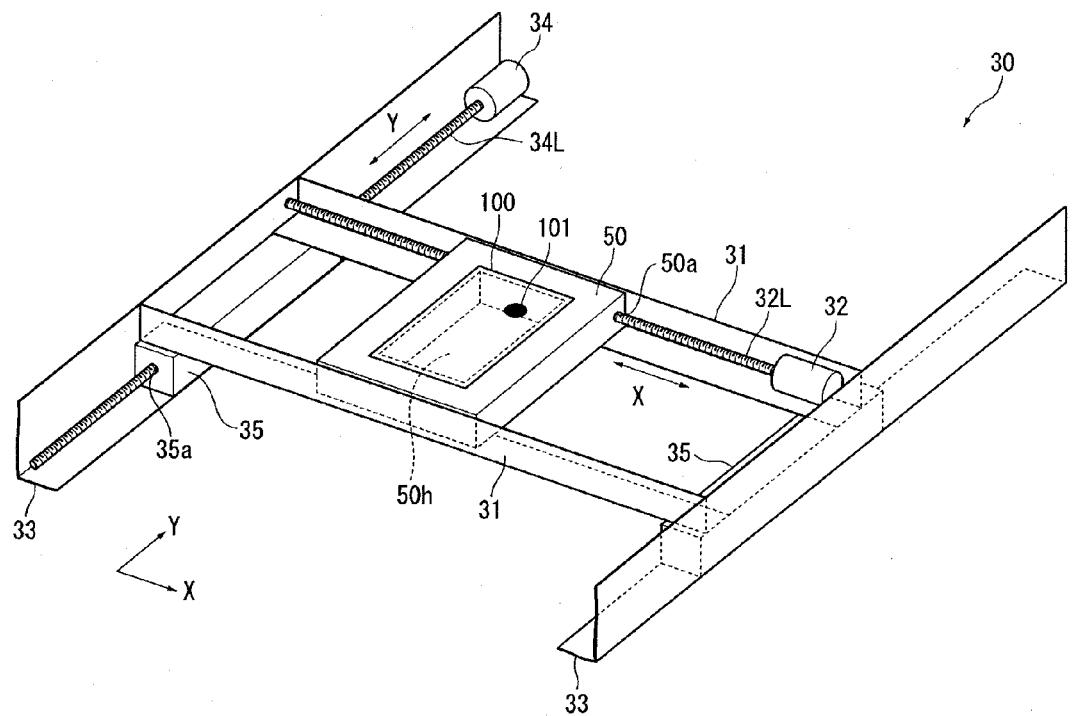
FIG. 2 is a perspective view illustrating configurations of a sample stage and a movement mechanism.

As illustrated in FIG. 2, the sample stage 50 is formed into the shape of a rectangular frame having an opening 50$h$ at its center, and the plate-shaped sample 100 is placed on the sample stage 50 so as to cover the opening 50$h$.

Two side edges of the sample stage 50 along an X-direction are placed on a pair of rails 31 each having an L-shaped cross-section so as to be interposed between the rails 31, and the sample stage 50 can move in the X-direction along the rails 31. One side of the sample stage 50 has a through-hole 50$a$ formed therein along the X-direction, and the inside of the through-hole 50$a$ is threaded. A feed screw 32L pivotally supported on a stepping motor 32 is threadedly engaged with the through-hole 50$a$, and the rotation of the stepping motor 32 allows the sample stage 50 to move back and forth in the X-direction along the rails 31.

Mounts 35 extending perpendicularly to the X-direction (that is, Y-direction) are fixed at both ends of the rails 31 on which the sample stage 50 is placed. The mounts 35 are interposed between a pair of rails 33 each having an L-shaped cross-section in the Y-direction, and the mounts 35 (and the sample stage 50) can move in the Y-direction along the rails 33. Further, one of the mounts 35 has a through-hole 35$a$ formed therein along the Y-direction, and the inside of the through-hole 35$a$ is threaded. A feed screw 34L pivotally supported on a stepping motor 34 is threadedly engaged with the through-hole 35a, and the rotation of the stepping motor 34 allows the mounts 35 (and the sample stage 50) to move back and forth in the Y-direction along the rails 33.

The rails 31, 33, the stepping motors 32, 34, the mounts 35, and the feed screws 32L, 34L constitute the movement mechanism 30. Further, the movement mechanism control means 61 described later adjusts the rotation amounts of the stepping motors 32, 34 to control the feed amounts of the feed screws 32L, 34L, thereby controlling the movement amount of the sample stage 50 in the X-Y directions.

Note that, the configuration of the movement mechanism 30 is not limited to the above-mentioned configuration, nor is the configuration of the sample stage 50 limited to the above-mentioned configuration.

Accordingly, the sample stage 50 (and the sample 100) can move in the X-Y directions, and the sample stage 50 moves relatively between an irradiation position 12R (see FIG. 4A, corresponding to a position where an optical axis 12c of the first X-ray source 12 crosses an XY plane) of the first X-ray source 12 and an irradiation position 22R (see FIG. 4A, corresponding to a position where the optical axis 22c of the second X-ray source 22 crosses the XY plane) of the second X-ray source 22, which are provided at separate positions on the XY plane.

Further, as illustrated in FIG. 1, in this embodiment, the optical axes 12c, 22c of the X-rays emitted from the first X-ray source 12 and the second X-ray source 22 are parallel to each other (Z-direction of FIG. 1), and the movement directions X-Y of the sample stage 50 are perpendicular to the optical axes 12c, 22c (Z-direction).

According to the above-mentioned configuration, the displacement of the sample stage 50 in the Z-direction becomes zero. Therefore, even when the sample stage 50 is moved in the X-Y directions, a distance h1 in the Z-direction between the first X-ray source 12 and the sample 100 and a distance h3 in the Z-direction between the second X-ray source 22 and the sample 100 can be invariably maintained at preset optimum values, and hence the measurement accuracy is not varied. Further, it is not necessary to provide a movement mechanism in the Z-direction.

Figure 3:
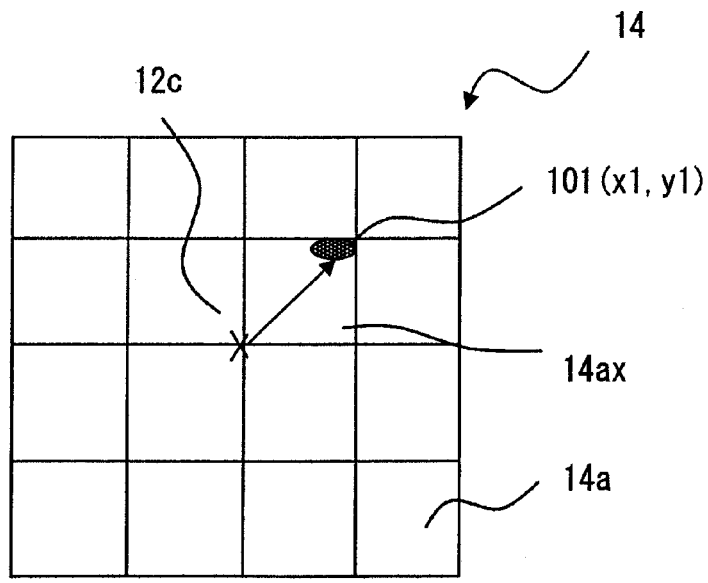
FIG. 3 is a diagram illustrating a method of calculating a foreign matter position through use of foreign matter position calculating means.

Next, a method of calculating the position of a foreign matter by the foreign matter position calculating means 60 is described with reference to FIG. 3. As illustrated in FIG. 3, individual solid-stage image pickup devices 14a constituting the transmission X-ray detector 14 receive light of an image obtained by converting the transmission X-ray 12x into fluorescent light, and two-dimensional information on the sample 100 is obtained. For example, in the case where the foreign matter 101 (e.g., Fe) is mixed in the sample 100 formed of a lithium cobaltate electrode plate, an X-ray transmission ratio for the foreign matter 101 (Fe) is lower than that for lithium cobaltate. This is because the X-ray transmission ratio is decreased by energy corresponding to an X-ray absorption end of Fe.

Therefore, of the solid-state image pickup devices 14a, a solid-state image pickup device 14ax at a position corresponding to the foreign matter 101 has a light reception amount smaller than those of the other solid-state image pickup devices 14a, and the foreign matter 101 becomes a dark part of an image to cause a contrast. Thus, image processing is performed by a known method for the part in which a contrast is caused, and accordingly the position of the foreign matter 101 on the surface of the sample 100 can be identified.

Note that, the foreign matter 101 can be identified as a region having a breadth, but alternatively, for example, known contour processing may be performed for the position of the foreign matter 101, and thereafter, the center of gravity of the contour may be considered as position coordinates of the foreign matter 101. For example, assuming that the position on the transmission X-ray detector 14 crossing the optical axis 12c of the second X-ray source 12 is a center (origin (0, 0)) of the sample 100, the coordinates (x1, y1) of the center of gravity of the foreign matter 101 can be considered as the position of the foreign matter 101.

Next, a method of controlling the position of the sample stage 50 (and the sample 100) by the movement mechanism control means 61 is described with reference to FIGS. 4A and 4B.

Figure 4A:
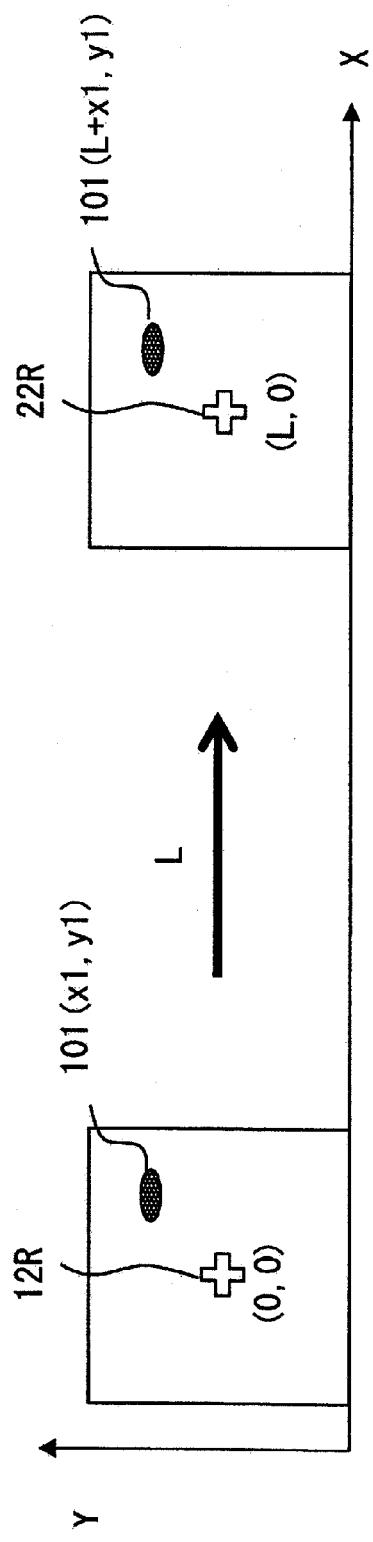
FIGS. 4A and 4B are diagrams illustrating a method of controlling the position of the sample stage (and a sample) through use of movement mechanism control means.

FIG. 4A illustrates the movement of the sample stage 50 between the irradiation position 12R of the first X-ray source 12 and the irradiation position 22R of the second X-ray source 22 in the case where the position control of the sample stage 50 (and the sample 100) is not performed. In this case, the irradiation position 12R and the irradiation position 22R are set at the same position in the Y-direction so that the irradiation position 12R is placed at the center of the sample 100. Then, when the irradiation position 22R is set at the position at which the sample stage 50 is moved by a distance L in the X-direction from the irradiation position 12R, the irradiation position 22R coincides with the center of the sample 100.

However, the foreign matter 101 (x1, y1) is positioned on the upper right side from the center of the sample 100, and hence, the irradiation position 22R (L, 0) of the second X-ray source 22 does not coincide with a position (L+x1, y1) of the foreign matter 101. Thus, the foreign matter 101 cannot be analyzed for elements by the fluorescent X-ray inspecting portion 20.

Figure 4B:
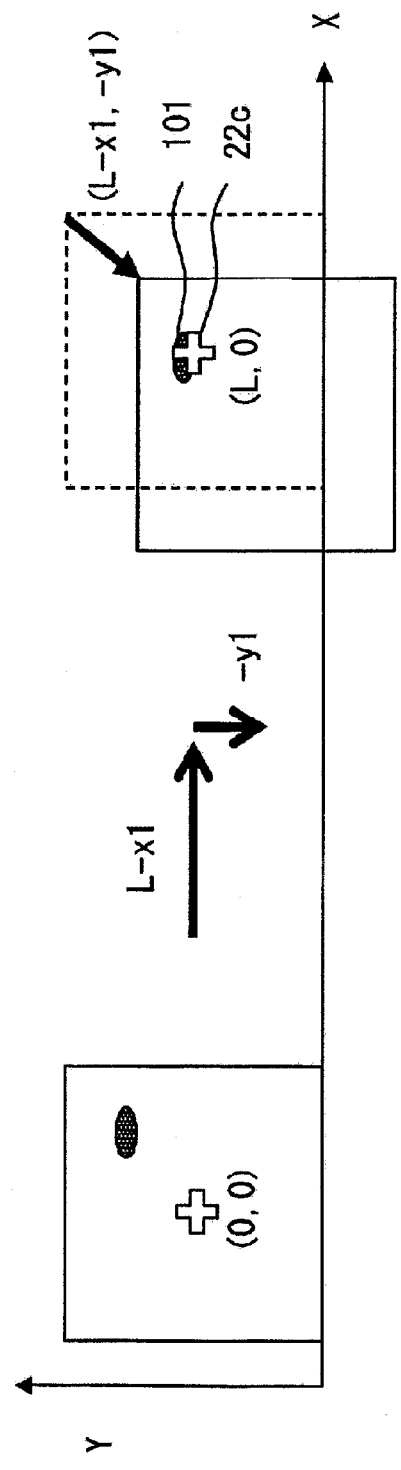

Accordingly, as illustrated in FIG. 4B, the movement mechanism control means 61 sets the movement amount from the irradiation position 12R to the irradiation position 22R to be a value (L-x1, -y1), which is obtained by subtracting a displacement amount (x1, y1) of the foreign matter 101 from the center of the sample 100. Thus, the position of the moved foreign matter 101 becomes (L+x1, y1)-(x1, y1)=(L, 0), which coincides with the irradiation position 22R. Thus, the position of the foreign matter 101 can be accurately and automatically irradiated with the X-ray 22x from the second X-ray source 22, and the foreign matter 101 can be analyzed for elements rapidly by the fluorescent X-ray inspecting portion 20.

Note that, a method of causing the position of the foreign matter 101 to coincide with the irradiation position (optical axis) 22c is not limited to the above-mentioned method.

Figure 5:
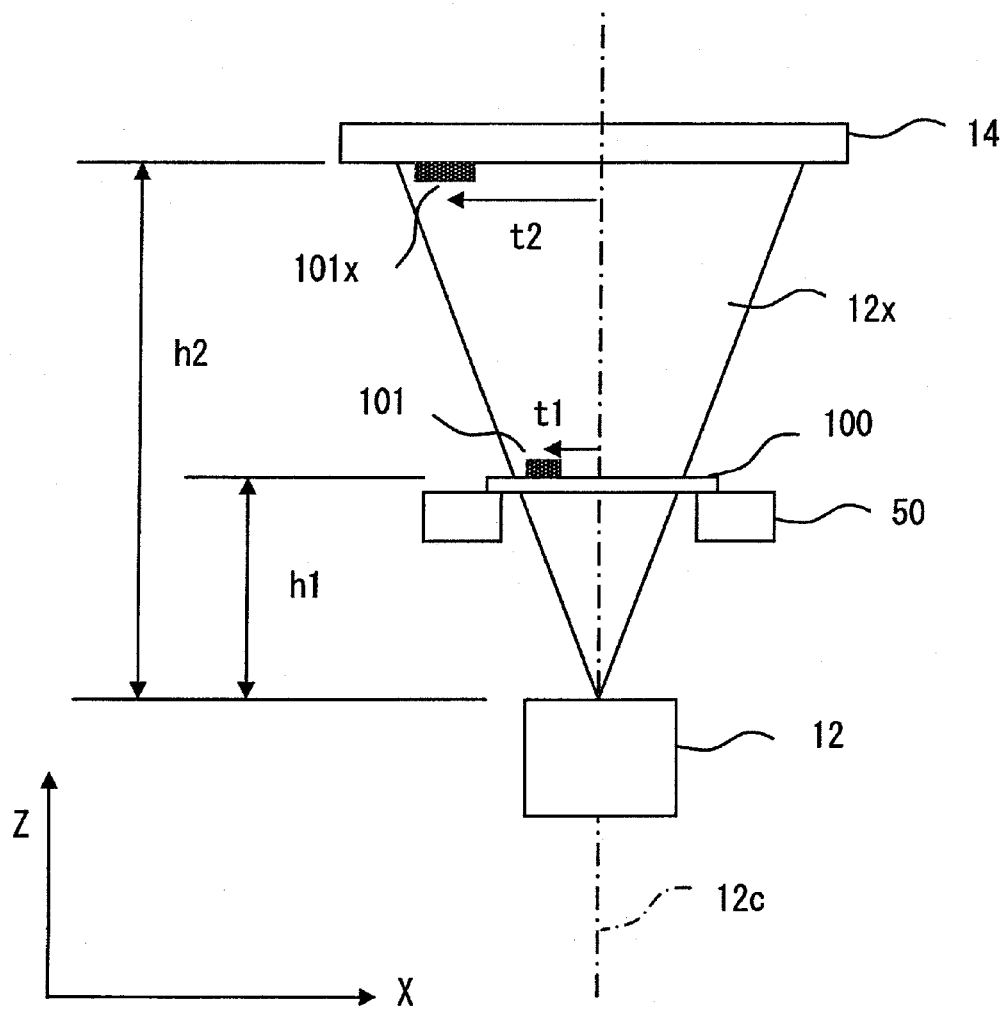
FIG. 5 is a diagram illustrating a method of determining the position of a foreign matter more accurately through use of the foreign matter position calculating means.

Next, a method of determining the position (x1, y1) of the foreign matter 101 more accurately by the foreign matter position calculating means 60 is described with reference to FIG. 5. As illustrated in FIG. 5, the transmission X-ray 12x spreads from the first X-ray source 12, and the foreign matter 101 on the sample 100 is shifted by t1 in the X-direction from the optical axis 12c. On the other hand, an image 101x is shifted by t2 in the X-direction from the optical axis 12c on the transmission X-ray detector 14, on which the image 101x is formed by a transmission X-ray output from the foreign matter 101.

Assuming that the distance in the Z-direction between the X-ray source 12 and the sample 100 (foreign matter 101) is h1 and the distance in the Z-direction between the X-ray source 12 and the transmission X-ray detector 14 is h2, the image 101x is an image obtained by enlarging the foreign matter 101 on the sample 100 by a coefficient of h2/h1, and hence, geometrically, the accurate shift amount t1 of the foreign matter 101 in the X-direction becomes (h1/h2)×t2. Thus, the foreign matter position calculating means 60 can determine a position (x1, y1)×(h1/h2) of the foreign matter 101 with high accuracy by multiplying the position of the image 101x obtained on the transmission X-ray detector 14 by the correction coefficient (h1/h2).

The same applies to determination of the position of the foreign matter 101 in the Y-direction.

It is to be understood that the present invention is not limited to the embodiment described above, and that the scope of the present invention encompasses various modifications and equivalents included in the idea and the scope of the present invention.

What is claimed is:

1. An X-ray analyzer, comprising:
   a transmission X-ray inspecting portion comprising:
      a first X-ray source; and
      a transmission X-ray detector for detecting a transmission X-ray that passed through a sample from the first X-ray source;
   a fluorescent X-ray inspecting portion comprising:
      a second X-ray source; and
      a fluorescent X-ray detector for detecting a fluorescent X-ray output from the sample when the sample is irradiated with an X-ray from the second X-ray source;
   a sample stage for holding the sample;
   a movement mechanism for moving the sample stage relatively between an irradiation position of the first X-ray source and an irradiation position of the second X-ray source;
   foreign matter position calculating means for calculating a position of a foreign matter detected in the sample by the transmission X-ray detector, the foreign matter position calculating means being configured to:
   calculate a distance t2 on the transmission X-ray detector along a direction perpendicular to an optical axis of the first X-ray source from the optical axis of the first X-ray source to the position of the foreign matter, a distance h1 parallel to the optical axis of the first X-ray source from the first X-ray source to the position of the foreign matter, and a distance h2 parallel to the optical axis of the first X-ray source from the first X-ray source to a position of the transmission X-ray detector; and
   calculate a distance t1 along a direction perpendicular to the optical axis of the first X-ray source from the optical axis of the first X-ray source to the position of the foreign matter based on an equation $t1=(h1/h2) \times t2$; and
   movement mechanism control means for controlling the movement mechanism so that the position of the foreign matter calculated by the foreign matter position calculating means coincides with an optical axis of the second X-ray source.

2. An X-ray analyzer according to claim 1,
   wherein the optical axis of the first X-ray source and the optical axis of the second X-ray source are parallel to each other, and
   wherein a movement direction of the sample stage is perpendicular to the optical axis of the first X-ray source and the optical axis of the second X-ray source.

3. An X-ray analysis method, comprising;
   detecting, using a transmission X-ray detector, a transmission X-ray that passed through a sample from a first X-ray source;
   detecting, at a position different from an irradiation position of the first X-ray source, a fluorescent X-ray output from the sample when the sample is irradiated with an X-ray from a second X-ray source;
   calculating a position of a foreign matter detected in the sample in the detecting a transmission X-ray by calculating a distance t2 on the transmission X-ray detector along a direction perpendicular to an optical axis of the first X-ray source from the optical axis of the first X-ray source to the position of the foreign matter, a distance hi parallel to the optical axis of the first X-ray source from the first X-ray source to the position of the foreign matter, and a distance h2 parallel to the optical axis of the first X-ray source from the first X-ray source to a position of the transmission X-ray detector, and calculating a distance ti along a direction perpendicular to the optical axis of the first X-ray source from the optical axis of the first X-ray source to the position of the foreign matter based on an equation $t1=(h1/h2) \times t2$; and
   moving the sample so that the position of the foreign matter coincides with an optical axis of the second X-ray source in the detecting a fluorescent X-ray.

\* \* \* \* \*